US011712667B2

(12) United States Patent
Sharma et al.

(10) Patent No.: US 11,712,667 B2
(45) Date of Patent: Aug. 1, 2023

(54) ANTI-MICROBIAL METAL COATINGS FOR FILTERS

(71) Applicant: Applied Membrane Technology, Inc., Minnetonka, MN (US)

(72) Inventors: Ashok K. Sharma, Hopkins, MN (US); Stephen P. Conover, Minneapolis, MN (US)

(73) Assignee: Applied Membrane Technology, Inc., Minnetonka, MN (US)

(*) Notice: Subject to any disclaimer, the term of this patent is extended or adjusted under 35 U.S.C. 154(b) by 35 days.

(21) Appl. No.: 17/209,970

(22) Filed: Mar. 23, 2021

(65) Prior Publication Data
US 2022/0305444 A1 Sep. 29, 2022

(51) Int. Cl.
| | |
|---|---|
| B01D 69/02 | (2006.01) |
| A61L 9/014 | (2006.01) |
| C02F 1/44 | (2023.01) |
| C02F 1/50 | (2023.01) |
| C23C 22/06 | (2006.01) |
| C23C 22/76 | (2006.01) |
| A61L 2/238 | (2006.01) |
| A61L 101/26 | (2006.01) |
| A61L 15/44 | (2006.01) |
| A61L 15/18 | (2006.01) |
| B01D 71/02 | (2006.01) |
| B01D 67/00 | (2006.01) |
| A61L 15/20 | (2006.01) |

(52) U.S. Cl.
CPC ............ *B01D 69/02* (2013.01); *A61L 2/238* (2013.01); *A61L 9/014* (2013.01); *B01D 67/009* (2013.01); *B01D 67/0093* (2013.01); *B01D 71/022* (2013.01); *C02F 1/44* (2013.01); *C02F 1/50* (2013.01); *C23C 22/06* (2013.01); *C23C 22/76* (2013.01); *A61L 15/18* (2013.01); *A61L 15/20* (2013.01); *A61L 15/44* (2013.01); *A61L 2101/26* (2020.08); *A61L 2209/14* (2013.01); *B01D 2325/48* (2013.01); *C02F 2303/04* (2013.01)

(58) Field of Classification Search
CPC .......... C23C 22/05; C23C 22/06; C23C 22/00
See application file for complete search history.

(56) References Cited

U.S. PATENT DOCUMENTS

| | | | |
|---|---|---|---|
| 4,252,838 A | 2/1981 | Boord et al. | |
| 4,717,587 A | 1/1988 | Suhr et al. | |
| 4,824,444 A | 4/1989 | Nomura | |
| 5,516,458 A | 5/1996 | Lelental et al. | |
| 6,136,389 A | 10/2000 | Conover et al. | |
| 6,919,035 B1 | 7/2005 | Clough | |
| 7,258,899 B1 | 8/2007 | Sharma et al. | |
| 7,666,494 B2 | 2/2010 | McClure et al. | |
| 2006/0284325 A1 | 12/2006 | Kohama et al. | |
| 2007/0184208 A1* | 8/2007 | Sharma | C23C 18/145 427/532 |
| 2001/0230339 | 9/2011 | Mann et al. | |
| 2011/0230339 A1* | 9/2011 | Mann | B01J 20/3236 423/592.1 |
| 2013/0274426 A1 | 10/2013 | Sugiura et al. | |

FOREIGN PATENT DOCUMENTS

GB 2547180 A * 8/2017 ........... C01G 23/053

OTHER PUBLICATIONS

Li et.al, The room temperature electron reduction for the preparation of silver nanoparticles on cotton with high antimicrobial activity, Carbohydrate Polymers, vol. 161, 2017, pp. 270-276, ISSN 0144-8617, https://doi.org/10.1016/j.carbpol.2017.01.020. (Year: 2017).*
Root, et.al, Conductive layers through electroless deposition of copper on woven cellulose lyocell fabrics, Surface and Coatings Technology, vol. 348, 2018, pp. 13-21, ISSN 0257-8972, https://doi.org/10.1016/j.surfcoat.2018.05.033. (Year: 2018).*
Szekeres, et.al, Copper-Coated Cellulose-Based Water Filters for Virus Retention Zoltán Németh, Krisztina Schrantz, Krisztián Németh, Mateusz Schabikowski, Jacqueline Traber, Wouter Pronk, Klára Hernádi, and Thomas Graule, ACS Omega 2018 3 (1), 446-454, DOI: 10.1021/acsomega.7b01496 (Year: 2018).*
Sen et al., "Electroceutical Fabric for PPE against COVID-19", pp. 1-31, accessed 2020.
Forbes, Allison Gasparini, "New Research Shows Electroceutical Fabric Eradicates Coronavirus Infectivity on Contact", Web page <https://www.forbes.com/sites/allisongasparini/2020/05/24/new-research-shows-electroceutical-fabric-eradicates-coronavirus-infectivity-on-contact/?sh=62b9ff021776>, 4 pages, May 24, 2020.
Scientific American, Rachel Crowell, "Electrified Fabric Could Zap the Coronavirus on Masks and Clothing", Web page <https://www.scientificamerican.com/article/electrified-fabric-could-zap-the-coronavirus-on-masks-and-clothing/>, 15 pages, Jun. 24, 2020.
INDYSTAR., Shari Rudavsky, "IU scientist discovers that face masks made from special fabric could kill the coronavirus", Web page <https://www.indystar.com/story/news/health/2020/05/26/iu-scientists-fabric-can-kill-coronavirus-could-lead-better-masks/5240152002/>, 3 pages, May 26, 2020.
Elsvier B.V., Li et al., "Fabrication of CuO nanofibers via the plasma decomposition of Cu(OH)2", Materials Letters 33, pp. 188-190, Oct. 1, 2008.

(Continued)

Primary Examiner — Bradley R Spies
Assistant Examiner — Jeannie McDermott
(74) Attorney, Agent, or Firm — Billion & Armitage

(57) ABSTRACT

An anti-microbial metal coating may be applied to filter membranes for use in actively depressing microbial viability in filtration applications. The anti-microbial metal coating may be applied to substrates that are considered to be sensitive to damage by conventional metal coating techniques or resistant to metal bonding. The coating may be applied from a salt absorbed to the substrate in solution, converted to a reducible form with a conversion agent, and reduced to active metal format through a low temperature plasma treatment.

12 Claims, No Drawings

(56) References Cited

OTHER PUBLICATIONS

Chemistry World, Rachel Brazil, "Developing antiviral mask technology in a pandemic", Web page <https://www.chemistryworld.com/news/developing-antiviral-mask-technology-in-a-pandemic/4011883.article>, 6 pages, Jun. 2, 2020.

Kas et al., "Three-dimensional porous hollow fibre copper electrodes for efficient and high-rate electrochemical carbon dioxide reduction", Nature Communications, pp. 1-7, Feb. 18, 2016.

Frontiers in Chemistry, Liu et al., "Dual-Function Conductive Copper Hollow Fibers for Microfiltration and Anti-biofouling in Electrochemical Membrane Bioreactors", Web page <https://www.frontiersin.org/articles/10.3389/fchem.2018.00445/full>, 18 pages, Sep. 25, 2018.

MDPI, Ligneris et al., "Mixed Matrix Poly(Vinyl Alcohol)-Copper nanofibrous Anti-Microbial Air-Microfilters", membranes, pp. 1-14, Jul. 17, 2019.

ACS Author Choice, Szekeres et al., "Copper Coated Cellulose-Based Water Filters for Virus Retention", ACS, Omega, pp. 446-454, Jan. 16, 2018.

American Society for Microbiology, Santo et al., "Bacterial Killing by Dry Metallic Copper Surfaces", Web page <https://aem.asm.org/content/77/3/794>, 21 pages, 2011.

MDPI, Formoso et al., "Electro-Conductive Membranes for Permeation Enhancement and Fouling Mitigation: A Short Review", membranes, pp. 1-24, Jul. 28, 2017.

Chua et al., "Face Masks in the New COVID-19 Normal: Materials, Testing, and Perspectives", AAAS Research, vol. 2020, pp. 1-40, 2020.

Wiley-VCH GMBH & Co. KGAA, Weinhein, Luan et al., "Plasma_strengthened Lithiophilicity of Copper Oxide Nanosheet-Decorated Cu Foil for Stable Lithium Metal Anode", Advanced Science, pp. 1-2, 2019.

Vinh Tien Nguyen and Khanh Son Trinh, "In Situ Deposition of Copper Nanoparticles on Polyethylene Terephal Filtering and Antibacterial Testing Against *Escherichia coli* and *Salmonella enterica*", Brazilian Journal of Chemical Engineering, vol. 36, No. 40, pp. 1553-1560, 2019, Brazil.

Elsevier B.V., Y. Li, P. Kuai, C. Liu, "Fabrication of CuO nanofibers via the plasma decomposition of $Cu(OH)_2$", Materials Letters 63, pp. 188-190, Oct. 1, 2008.

3M, "Respiratory Protection for Airborne Exposures to Biohazards", Technical Data Bulletin, pp. 1-10, Jun. 5, 2020.

Vizient, "COVID-19 guide to face amsks and filtering facepiece respirators", Web page <https://www.vizientinc.com/covid-19/covid-19-mask-and-respirator-guide>, 8 pages, Aug. 3, 2020, retrieved from Internet Archive Wayback Machine <https://web.archive.org/web/20200803200351/https://www.vizientinc.com/covid-19/covid-19-mask-and-respirator-guide> on Mar. 22, 2021.

Elsevier Ltd., Khoo et al., "Ultra-portable low-cost improvised powered air-purifying respirator: feasibility study", Elsevier Public Health emergency Collection, 7 pages, May 7, 2020.

ACS Publications, Karuri et al.,"A Novel Anaerobic Electrochemical Membrane Bioreactor (AnEMBR) with Conductive Hollow-fiber Membrane for Treatment of Low-Organic Strength Solutions", Enviornmental Science & Technology, pp. A-I, Oct. 13, 2014.

Smart Seperation Ltd, "mTAP KER01: Antiviral filter developed by Smart Separations to sanitise air and water and potential to protect surfaces", <https://ec.europa.eu/info/funding-tenders/opportunities/portal/screen/opportunities/horizon-results-platform/22901>, 5 pages, Apr. 29, 2020.

ACS Publications, El-Atab et al., "Flexible nanoporous Template for the Design and Development of Reusable Ant-COVID-19 Hydrophobic Face Masks", Web page <https://pubs.acs.org/doi/10.1021/acsnano.0c03976>, ACS NANO, 22 pages, May 20, 2020.

V. A. Liu, W. E. Jastromb, S. N. Bhatia, "Engineering portein and cell adhesivity using PEO-terminated triblock polymers", <https://pubmed.ncbi.nlm.nih.gov/11835168/>, Journal of Biomedical Materials Research, vol. 60, Issue 1, pp. 126-134, Jan. 23, 2002.

Roosjen et al., "Stability and effectiveness against bacterial adhesion of poly(ethlene oxide) coatings in biological fluids", Journal of Biomedical Materials Research, vol. 73B, Issue 2, pp. 347-354, Feb. 25, 2005.

Dinsa Sachan, "COVID-19 pandemic has spurred materials researchers to develop antiviral masks", <https://pubs.acs.org/doi/10.1021/acscentsci.0c01172>, C&EN, vol. 98, Issue 31, 8 pages, Aug. 12, 2020.

International Fiber Journal, "COVID-19 Update: INDA publishes Meltblown Nonwoven Markets: COVID-19 Impact Analysis", <https://fiberjournal.com/covid-19/>, 88 pages, Aug. 5, 2020.

Patrick Mize, "Durable Visible Light-activated Antiviral Coatings for Fabrics Used for Personal", <https://www.sbir.gov/sbirsearch/detail/193279>, 3 pages, accessed Mar. 22, 2021.

Centers for Disease Control and Prevention, "Considerations for Optimizing the Supply of Powered Air-Purifying Respirators (PAPRs)", <https://www.cdc.gov/coronavirus/2019-ncov/hcp/ppe-strategy/powered-air-purifying-respirators-strategy.html>, 12 pages, Apr. 19, 2020.

Raumedic, "Antimicrobial Materials", <https://www.raumedic.com/us/technologies/material-expertise/antimicrobial-materials>, 2 pages, accessed Mar. 23, 2021.

International Search Report and Written Opinion dated Jul. 6, 2022 and issued in International Patent Application No. PCT/US2022/20691.

\* cited by examiner

ANTI-MICROBIAL METAL COATINGS FOR FILTERS

FIELD OF THE INVENTION

The present invention relates to substrate coatings generally, and more particularly methods for obtaining metal coatings on substrates for anti-microbial filtration and other applications. The methods of the present invention may be particularly suitable for porous substrates that are susceptible to damage when processed through conventional metallization techniques.

BACKGROUND OF THE INVENTION

Metals are known for their anti-microbial properties. Copper and silver have long been used to purify water and to preserve perishable food items. More recently, titanium, platinum, palladium, zinc, and other metals have also been explored for their anti-microbial properties. Copper and silver remain popular as anti-microbial agents due to their relatively low cost and high bioavailability.

Copper and copper alloys have gained renewed importance in recent years for use in neutralizing viruses that are harmful to the human population, including the coronavirus that causes COVID-19. To date, however, no effective technique has been developed to incorporate metals such as copper in personal protection equipment (PPE) or filters for air or water disinfection, although it is well known to coat metal with polymeric materials to improve performance, corrosion resistance and longevity. Filter membranes prepared by incorporating pulverized metal or metal salts in polymer matrices, for example in polymer solutions or melts before spinning into fibers have found limited success because a large percentage of the metal remains embedded in the bulk of the polymer.

Sputtering, physical vapor deposition (PVD), and chemical vapor deposition (CVD) have been widely used for depositing metal films onto various substrates. Each technique, however, has challenges for use in connection with microporous plastic substrates. Physical vapor deposition typically requires extremely low pressure environments and/or expensive coating equipment, since the metals need to be vaporized. Chemical vapor deposition and sputtering techniques may be performed at somewhat higher pressure environments, but are more suited for coating extremely thin films of silicon, gallium, arsenide, and the like on silicon wafers used in the semiconductor industry. When used on porous plastic substrates, textures and residual stresses may arise in sputtered metal layers that can result in the deformation of the sensitive membrane structure. Moreover, CVD and sputtering techniques are not generally suited for continuous application, such as in producing metal-coated HEPA filters.

U.S. Pat. Nos. 4,252,838 and 4,717,587 provide a method of producing metallic structures on nonconductive substrates by glow discharge disintegration of volatile organometallic complexes for semiconductor applications. The technique, however, is useful only for depositing metals that form volatile complexes. Such complexes are not only expensive but also produce a very low yield of metal as the majority of the complex is lost unconverted in the vacuum process.

U.S. Pat. No. 5,516,458 describes a method for depositing an antistatic metal containing transparent coating on thermal imaging films by applying a source of metal mixed in a polymeric film former liquid composition followed by glow discharge treatment at very low pressure of $10^{-5}$ mbar. The resultant coating had surface resistivities ranging from $10^8$-$10^{13}$ ohms/□. Such a technique will not be useful for preparing antimicrobial metal coating on microporous substrates as the polymeric film former will block the pores of the substrate.

U.S. Pat. No. 7,258,899 describes a method for coating metals on microporous substrates based on polypropylene, polyvinylidene fluoride, polytetrafluoroethylene, ceramics, and the like by applying a coating of organometallic complex of metal dissolved in organic solvents such as toluene, xylene, acetone, and alcohol by dip coating, followed by reduction of the organometallic complex to metal by low pressure plasma. The method, however, suffers from the disadvantage that many organometallic complexes are highly volatile and not suited for plasma reduction, which is often performed at low pressures. Many others are not readily soluble in organic solvents.

U.S. Pat. No. 7,666,494 B2 provides a method for producing metallic nanoparticles on a microporous substrate that are subsequently transferred to other substrates such as glass, plastic and metals for imparting special optical, magnetic and chemical properties for application in infrared detectors, sensors and optical switching devices. The metal nanoparticles are created by physical vapor deposition such as electron beam evaporation or sputtering. The process operates at ultrahigh vacuum and the deposited nanoparticles are only physically held in the microporous substrate which acts as a storage vessel for the metal.

Attempts have been made to apply metal salts to substrates followed by reduction of the salt to metal by strong chemical reducing agents such as ascorbic acid or sodium borohydride, which can result in substantial reduction in the tensile strength of the substrates. Another recently reported method involves the application of a composite metallic ink comprising a metal salt, a binder, and a reducing agent to a microporous substrate by dip coating. The coated substrate is heated to convert the metal salt into a sintered metal coating. This method, however, uses toxic chemicals, requires heat, has the tendency to block substrate pores, and is therefore not suited for sensitive membrane substrates.

There is therefore a need for an efficient and inexpensive process for coating cellulosic and non-cellulosic polymers with active metal species that possess effective anti-microbial properties.

SUMMARY OF THE INVENTION

By means of the present invention, metal salts, both organic and inorganic, may be deposited on a porous substrate surface and chemically converted to insoluble oxides or hydroxides while at the substrate, and reduced to an active metal form without significant change in the porosity or tensile strength of the substrate. The reduction may be performed by a low-temperature plasma process in a continuous, semi-continuous, or batch operation. Through this process, the metal activity is primarily retained at the substrate surface, and typically in a nanoparticle form. The anti-microbial metal coatings of the present invention may find application in PPE, air and water filtration membranes, and in wound healing dressings. These metal coated membranes can also find application in reaction catalysis, in bioreactors for waste water treatment, microbial fuel cells, biosensors, electroceutical fabrics, electrochemical processes, antifouling area waste filters, solar cells, supercapacitors, batteries, membrane distillation, evaporative membrane applications, and in the design of smart textiles.

In an embodiment of the invention, a metal is coated onto a substrate by applying a metal solution to the substrate, wherein the metal solution includes a solvent and a metal component selected from one or more inorganic or organic metal salts that are soluble in the solvent. The metal component solution is reacted at the substrate with a conversion agent to form an insoluble metal hydroxide or a metal oxide, which is then exposed to a plasma environment at ambient temperature and less than 100 KPa pressure to reduce the metal hydroxide or metal oxide to a metal coating at the substrate.

In an embodiment wherein the metal component solution includes water as the solvent, the metal component may include one or more water soluble metal salts. The one or more water soluble metal salts may be selected from at least one of a sulfate, nitrate, nitrite, carbonate, bicarbonate, chloride, chlorate, arsenate, phosphate, formate, acetate, and propiontae. The substrate in this embodiment may be cellulose-based, ceramic, or porous substrates such as Polybenzimidazole or polyethersulfone.

In an embodiment wherein the metal component solution includes an organic solvent, the metal component may include an organometallic complex of metal, optionally with oxygen linkage such as an acetylacetonoate, a perfluoroacetate, or a fluoroacetylacetonate. In some embodiments, the organometallic complex of metal is selected from at least one of copper acetylacetonate, copper trifluoro acetylacetonate and silver trifluoroacetate. In preferred embodiments, the metal complex is converted to a hydroxide or oxide which is stable and reducible to metal under plasma conditions.

In an embodiment, the metal component solution may be applied to the substrate by spray coating, roller coating, brush coating, or dip coating.

In an embodiment, the conversion agent is selected from at least one of a hydroxide of alkali metal.

In an embodiment, the reactive metal layer on the substrate may be heated by applying a low electric voltage which can further deactivate microbes, regenerate the substrate, and accelerate the rate of physical, chemical or biochemical reaction.

In an embodiment, the plasma environment is generated by applying electromagnetic energy in a glow zone between spaced apart electrodes in the presence of a plasma supporting gas or gas blends selected from argon, hydrogen, krypton, xenon, helium, nitrogen, and oxygen. The electromagnetic energy may be applied at 13.56 MHz.

DETAILED DESCRIPTION OF THE PREFERRED EMBODIMENTS

An object of the invention is to provide metallic coatings on porous substrates from simple inorganic and organic metal components through low-temperature plasma conversion of their hydroxides and oxides to metal. Solutions containing metal components are applied to the substrates, with the metal components being chemically converted with a suitable conversion agent to the metal hydroxides or metal oxides. Exposure of the metal hydroxides or metal oxides to ambient temperature plasma under mild operating conditions produce active metal coatings useful for many applications including anti-microbial products.

A particular object of the invention is to provide metallic coatings on porous substrates that are susceptible to damage from conventional metal coating techniques. Example substrates suitable for the metallic coating process of the present invention include materials such as regenerated base filter paper, glass filters, personal protection equipment based on cotton fabric, nonwoven cotton dressings, water filtration candles, and membranes based on ceramics and other water wettable polymers such as polyethersulfone (PES) and polybenzimidazole, as well as filter membranes based on other polymers such as polypropylene, polyethylene, polyvinylidene fluoride, and nylon.

Use of active plasma for reducing adsorbed metal complexes to thin films of metals has been demonstrated by the present inventors in U.S. Pat. No. 6,136,389, as well as in U.S. Pat. No. 7,258,899, the contents of which being incorporated herein by reference in their entireties.

When coated onto fibers, tubular membranes, or flat substrates, coatings created pursuant to the present invention may serve in a variety of applications, as described above.

The plasma treatment of the coated substrate may be achieved using a known plasma reactor. A capacitively coupled tubular reactor operating at 13.56 MHz may be employed in the plasma reductions described herein. Custom-designed reactors may be utilized if required for continuous coating of substrates such as hollow fiber and films. One such reactor is described in U.S. Pat. No. 4,824,444.

The chosen substrate may be contacted with the metal component solution by any suitable means such as spray coating, brush coating, dip coating, roller coating, sponge coating, and the like. The selected substrate is preferably wettable by the metal component solution, wherein the surface tension of the metal component solution is lower than the surface energy of the substrate, so that the liquid is able to maintain contact with the substrate. In the case of substrates which do not readily wet upon contact with the selected metal component solution, chemical and physical methods including a preliminary exposure to a suitable plasma surface treatment may be used to enhance the wettability and spreadability of the metal component solution onto the surface and/or into the substrate pores.

The metal component solution includes a solvent and a metal component selected from one or more metal salts or one or more organometallic complexes of metal. Example water-soluble salts include sulfates, nitrates, nitrites, arsenates, arsenites, chlorides, chlorates, formates, acetates, propionates, carbonates, and bicarbonates. Aqueous solutions of water-soluble metal salts may be preferred for application to polar substrates, such as cellulose-based substrates. It is contemplated that one or more metal combinations, alloys, mixtures, and metal complexes may be employed in the metal coatings of the present invention. Example water-soluble salts useful in the present invention include inorganic salts of copper, silver, cobalt, tin, zinc, palladium, and nickel. Organometallic complexes and organic salts of metals may be used in organic solvents such as methanol, ethanol, or other suitable solvents to form the metal component solution. Example organic solvent-soluble organic salts of metal include silver trifluoroacetate, and organometallic complexes of metals include copperacetylacetonate, copper trifluoroacetylacetonate and silver trifluoroacetyacetonate.

The metal component solution at the substrate is preferably reacted with a conversion agent to form a metal hydroxide or a metal oxide. The conversion reaction may be conducted in "wet" conditions, prior to solvent evaporation, or in the "dry" condition after solvent evaporation. The conversion agent is preferably a chemical that is reactable with the metal component solution to form a reducible water insoluble metal compound. In some embodiments, the conversion agent is a chemical that is reactable with the metal solution to form a metal hydroxide or oxide. Example conversion agents include hydroxides of alkali metals such as sodium hydroxide and potassium hydroxide.

Subsequent to the conversion reaction, the system may be washed free of excess conversion agent and dried, for example in an air-forced oven or in ambient conditions to evaporate the solvents, leaving the reducible metal compounds at the substrate surface.

The substrates are subsequently mounted in a plasma reactor, and the system evacuated to a pressure of less than 100 KPa. Example plasma treatment conditions include a plasma gas selected from argon, hydrogen, oxygen, blends of oxygen and nitrogen, blends of hydrogen and nitrogen, krypton, xenon, helium, and other plasma-excitable gases. The gas flow rate may be between 1-500 SCCM, preferably between 5-100 SCCM at a system pressure of less than 100 KPa, preferably less than 10 KPa, and more preferably between 0.001 KPa and 1 KPa. In some embodiments, the system pressure is between 0.01-0.1 KPa. The discharge power of the plasma system may be between 1-500 watts, and preferably between 5-150 watts, at 13.56 MHz for 15 seconds to 30 minutes.

The reduction to active metal at the substrate surface may begin nearly instantaneously upon exposure to the plasma environment. The plasma conditions described above are exemplary only, and may change depending upon the size of the reactor, substrate material, power, source, and plasma coupling mechanisms.

The substrates may be rotated during the plasma exposure for better uniformity and continuous web or fiber strands may be moved continuously through the plasma. After plasma treatment, vacuum is released using standard venting techniques.

The substrates may be re-exposed as well as re-coated and re-processed if additional metal coating is desirous or if initial coating was incomplete. Multiple layered coatings may also be readily accomplished by re-processing the substrates.

Alloys may be formed by suitable mixing of multiple metal component materials in compatible solvents. Deposition of the metal coatings may be manipulated for placement and coverage on the substrate, including though the use of masking techniques.

The metal coatings of the present invention may be considered conductive, and which exhibit a relatively low surface resistivity. The low surface resistivity may be facilitated by a continuous metal layer deposited on the substrate. In some embodiments, the continuous metal layer may be formed at the substrate so as to not interfere with the porosity of the substrate, wherein pores of the substrate are open through the metal coating. This is possible with a thin metal coating that is deposited on the substrate surface surrounding the pore opening, but does not cover the pore opening itself.

Certain applications of the metal coated substrates of the present invention may be benefited by a surface that is not electrically insulative. A "conductive" material is considered to have a surface resistivity of less than $1 \times 10^5$ Ω/□. A "dissipative" material is considered to have a surface resistivity of between $1 \times 10^5$ Ω/□ and $1 \times 10^{12}$ Ω/□. An "insulative" material is considered to have a surface resistivity of at least $1 \times 10^{12}$ Ω/□. Thus, in some embodiments, the metal coated substrate may preferably exhibit a surface resistivity of less than $1 \times 10^{12}$ Ω/□. In some embodiments, the metal coated substrate may preferably exhibit a surface resistivity of less than $1 \times 10^5$ Ω/□. In still further embodiments, the metal coated substrate may preferably exhibit a surface resistivity of less than $1 \times 10^3$ Ω/□. In some embodiments the metal coated substrate may preferably exhibit a surface resistivity of less than $1 \times 10^2$ Ω/□.

EXAMPLES

The following specific examples are provided as demonstrative of the techniques of the present invention.

Example 1

Copper sulfate pentahydrate (CSP) is soluble in water and can be easily absorbed on cellulosic substrates. The absorbed CSP can be hydrolyzed by sodium hydroxide to copper hydroxide, which can then be reduced to copper metal using the plasma treatment process. The copper metal remains absorbed in the fibril structure of the cellulosic substrate, and does not leach out easily in water.

Four drops of 25% w/v CSP solution in water were applied to Whatman No. 5 filter paper and allowed to dry in air for 12 hours followed by reaction with 1.5 N sodium hydroxide (NaOH) solution in a petri dish for one minute. The color of the drop impressions immediately changed from almost colorless to blue indicating conversion to copper hydroxide. Due to its very poor solubility in water, the copper hydroxide remained bonded to the filter paper, resulting in almost 100% conversion. The copper hydroxide coated filter paper was subsequently washed with water to get rid of free chemicals, and then dried in air at ambient temperature for 12 hours to offer a copper hydroxide coated substrate which was insensitive to water.

Example 2

The copper hydroxide coated Whatman #5 filter paper of Example 1 was treated with low pressure Argon (Ar) plasma generated at 40 mtorr for 3 minutes at 20 watts RF power. The conversion to metal started almost instantaneously. The converted metal coating exhibited a surface resistivity of 195Ω/□ (Ohms/square).

Example 3

The copper hydroxide coated substrate prepared in Example 1 above was treated with low pressure $Ar/H_2$ (Argon/Hydrogen) plasma for 6 minutes at 40 mtorr pressure and 20 watts RF power. The resultant metal coating exhibited a surface resistivity of 25Ω/□ and showed substantial anti-microbial property toward the E Coli K-12 strain (see the test method described in Example 17 and results in Table 1).

Example 4

A solution of 25% w/v of copper sulfate pentahydrate (CSP) in water was applied to a 4"×4" piece of 'hydro entangled Cellulose-Polyester' clean room wipe cloth (source: Amplitude Sigma) by immersing the wipe cloth in the solution. The soaked substrate was then immersed in 1.5 N NaOH solution for approximately 1 minute without allowing for drying in between the two treatments. The conversion to blue copper hydroxide was instantaneous. Once again due to very poor solubility of copper hydroxide in water, the converted salt remained bonded to the substrate, resulting in almost 100% conversion. The copper hydroxide coated substrate was subsequently washed with copious amount of water to dispose of free chemicals, and then dried in air at ambient temperature for 2 hours. The dried copper hydroxide coated substrate was treated with low pressure argon/hydrogen plasma generated at 13.56 MHz for 5 minutes at 50 W. The copper hydroxide coating was reduced to a dark brown coating of metallic copper. The metal-coated substrate exhibited a surface resistivity of 110Ω/□ and showed substantial anti-microbial activity toward the *E Coli* K-12 strain (see results in Table 1).

Example 5

A 3"×3" piece of cotton bandage (Johnson and Johnson) was coated with 25% w/v solution of CSP and converted to copper hydroxide as described in Example 4. The copper hydroxide was reduced to copper metal through the plasma treatment described as in the Example 4. The plasma treated cotton bandage exhibited a surface resistivity of 400Ω/□ from end to end, and showed substantial anti-microbial property toward the *E Coli* K-12 strain.

Example 6

A 10% w/v solution of silver nitrate in water was prepared and applied onto Whatman filter paper #5 by a dropper. The solution drops were allowed to dry for approximately 15 minutes in air and subsequently treated with 1.5 N sodium hydroxide solution in a petri dish for 30 sec. The colorless drops of silver nitrate immediately changed in color to brown indicating chemical conversion to Silver oxide. Argon plasma treatment of silver oxide at 125 mtorr, and 25 W RF power for 3 minutes lead to the formation of silvery coatings on the filter paper which exhibited a surface resistivity of 25Ω/□. Increasing the treatment time to 6 minutes lead to silver coating which exhibited a surface resistivity of 5Ω/□. The coating remained stable in water for 4 days and showed significant antimicrobial activity to *E. Coli* K-12 strain (see results in Table 1).

Example 7

A 10% solution of silver trifluoroacetate in ethyl alcohol solvent was applied to a cellulosic substrate. The dried clear coating of silver trifluoroacetate was treated with $Ar/H_2$ plasma at a pressure of 200 mtorr as in the earlier experiment which converted the silver trifluoroacetate to a dark brown coating, but surprisingly this coating was not electrically conductive and exhibited a very high surface resistivity. It appears that the trifluoroacetyl moiety in the structure of salt interferes with the metallizing mechanism under plasma.

Example 8

A 10% solution of silver trifluoroacetate in ethyl alcohol solvent was applied on to a cellulosic substrate followed by reaction with 2.5N NaOH solution, which converted the clear coating of silver trifluoroacetate into dark brown silver oxide. The coating was thoroughly washed with water and treated with Ar/H2 plasma at a pressure of 200 mtorr as in the earlier experiment which converted the oxide into a shiny conductive silver that exhibited a surface resistivity of 5 Ω/□.

Example 9

A 10% solution of silver trifluoroacetate in ethyl alcohol solvent was applied on to microporous polypropylene and polyether sulfone hollow fiber membranes using a dip coating apparatus, followed by reaction with 2.5N NaOH solution which instantaneously converted the silver salt to silver oxide. The coated substrates were treated with argon and/or hydrogen plasma as described in Example 4, to render a bluish brown conductive metal coating. Both coated substrates retarded the growth of the *E Coli* K-12 strain, as shown in Table 1.

Example 10

A solution of 7.5% w/v copper trifluoroacetylacetonate (CuTFAA) in ethanol was applied to Whatman Filter paper #5 in drop form. The coated substrates, after a very short evacuation time of 2 minutes, was treated with argon/hydrogen plasma as described in Example 4 to render a black metal coating. The coated Whatman #4 filter paper exhibited a surface resistivity of 300-400Ω/□, and retarded growth of the *E Coli* K-12 strain. This compound did not need conversion to hydroxide and or oxide because of labile metal-oxygen linkage in the structure. Longer evacuation time of 40 minutes (Sample 10A), however, led to loss of salt from the substrates due to low sublimation temperature of the copper complex and resulted in non-conductive, non-antimicrobial coatings.

Example 11

A solution of 7.5% w/v copper trifluoroacetylacetonate (CuTFAA) in ethanol was applied to Whatman Filter paper #5 by a dropper and allowed to dry. The coated substrate was treated with 2.5N NaOH solution for 2 minutes in a petri dish and after thorough washing in distilled water allowed to dry. Unlike the original organometallic complex, the converted salt was completely insoluble in alcohol. The dried hydrolyzed salt, after a long evacuation time of 60 minutes, was treated with Ar/H2 plasma as in the above experiments. The color of the coating immediately changed to black coating indicative of conversion to metal, which also demonstrated good antimicrobial activity. Conversion of volatile metal complex to nonvolatile hydroxide helped in improving its stability in vacuum.

Example 12

A 15% w/v solution of cobalt chloride hexahydrate (CCH) in water was prepared and applied onto Whatman filter paper #5 by a dropper. The solution drops were allowed to dry for approximately 15 minutes in air. The magenta color of CCH changed to deep blue on drying indicating conversion to the anhydrous form of the salt. The dried salt drops were subsequently treated with 1.5 N Sodium hydroxide solution in a petri dish for 30 sec. The bluish drops of anhydrous Cobalt chloride immediately changed to olive color indicating chemical conversion to cobalt hydroxide. Argon/Hydrogen plasma treatment of cobalt hydroxide at 125 mtorr, and 50 W RF power for 5 minutes lead to the formation of bluish black cobalt coatings on the filter paper. The coated substrate showed substantial anti-microbial property toward the *E Coli* K-12 strain.

Example 13

Blends of CSP (25% w/v) and CCH (15% w/v) were prepared by mixing the salt solutions in a 1:1 ratio. Strips of Whatman #5 filter paper were coated with the blend solution by the dipping process followed by short drying for approximately 15 minutes in air. The coated substrate was then treated with 1.25 N NaOH for approximately 1 minute followed by through washing in running tap water. The hydrolyzed coating was dried in air and subsequently treated with Argon/Hydrogen plasma as in earlier examples. The color of coating turned from pale bluish green to green black after metallization. Unlike the untreated salt the converted metal hydroxide and metal coatings were completely insoluble in water.

Example 14

A blend of CSP (25% w/v), CCH (15% w/v) and Nickel Chloride hexahydrate (NCH) (15% w/v) was prepared by mixing the aqueous salt solutions in 1:1:1 ratio. Strips of Whatman #5 filter paper were coated with the blend solution by the dipping process followed by short drying for approximately 15 minutes in air. The coated substrate was then treated with 1.25 N NaOH for approximately 1 minute followed by through washing in running tap water. The hydrolyzed coating was dried in air and subsequently treated with Argon/Hydrogen plasma as in earlier examples. The color of coating turned from bluish green to brownish green after metallization. Unlike the salt, the converted metal hydroxide and metal coatings were completely insoluble in water and exhibited substantial antimicrobial activity (see Table 1).

Example 15

Strips of Whatman #5 filter paper were coated with CSP solution of varying concentrations (25%, 10%, 5%, 2.5% and 1.0% w/v) by dipping method and dried in air. The dried salt on strips in each case was hydrolyzed in 1 N NaOH (samples a, b, c, d and e) for approximately 1 minute. In addition, the strips coated with 25% w/v CSP solution were also hydrolyzed in 1 N KOH, 0.5 NaOH and 0.2 NaOH solution (sample f, g and h). All hydrolyzed samples were thoroughly washed with deionized water and allowed to dry in air. The dried samples were subsequently treated by hydrogen/argon plasma as in the Example 4. All samples darkened on exposure to plasma with the color intensity proportional to the concentration of the CSP solution used. While samples a, b, f, g and h exhibited varying degree of surface resistivity as well as good antimicrobial resistance, the lower salt concentration coated sample exhibited no measurable conductivity with the meter employed. The lower metal concentration apparently had non-continuous coating of extremely high surface resistivity due to the large pore structures of the substrates. No significant difference was observed of using lower concentration of NaOH or KOH for hydrolysis.

Example 16

A cleaned 5 mm diameter CPG (controlled pore glass) tube, approx. 1 inch in length was dip coated with silver nitrate solution, 25% w/v in water, and allowed to dry in air. The coated CPG tube was treated with 1.25 N NaOH solution for converting silver nitrate salt to Silver oxide. The substrate was washed in flowing tap water and dried in air. The Silver oxide coated CPG was subsequently treated with Argon/Hydrogen plasma at 100 W for 3 minutes. The resultant metal coating offered a surface resistivity of 200Ω/□, indicating that the salt had been converted to metal.

Example 17

Metal coatings prepared in some of the examples above were tested for their antimicrobial activity by placing them on a pre-poured LB agar plate inoculated with *E. Coli* (stain K12 cultured in TSB). The plates were left in the culture oven at 35 deg C. for 16-18 hours. The width of the resulting zone of inhibition from the edge of sample to the edge of bacterial colonies, was noted in each case. In a few instances, the experiment was repeated with metal coatings kept immersed in water for 96 hours to see the effect of coating exposure to water. The results summarized in table confirmed that the metal coating prepared by this method exhibited a zone of retarded bacterial growth and coatings retained their efficacy even after exposure to water.

TABLE 1

| Example # | Metal | Metal Concentration | Zone of Inhibition | Zone of Inhibition after exposure to water |
|---|---|---|---|---|
| Example 3 | Copper | 25% | 10 mm | NA |
| Example 4 | Copper | 25% | 4 mm | NA |
| Example 6 | Silver | 10% | 6 mm | 4 mm |
| Example 9 | silver | 10% | 4 mm | NA |
| Example 10 | Copper | 7.5% | 2 mm | NA |
| Example 10A | Copper | 7.5% | — | |
| Example 11 | Copper | 7.5% | 1.5 mm | NA |
| Example 12 | Cobalt | 15% | 2 mm | NA |
| Example 14 | Cobalt+ Copper+ Nickel | 15% | 1 mm | NA |
| Example 15 | Copper | 25% | 2 mm | 1 mm |
| Example 15 | Copper | 10% | 1 mm | 1 mm |

Example 18

A 12 ml vial was filled with the broth solution and inoculated with 50 ul *E Coli* bacteria. Whatman filter strips coated with metals were immersed in the broth and allowed to culture at 37° C. The optical density of the solution at 600 nm was measured at 1 hour, 2 hours and 120 hours duration. The results summarized below confirmed that both copper and silver metal coating prepared by this method retarded the growth of *E. Coli* in solution.

TABLE 2

| Example | OD at 5 minutes | OD at 1 hour | OD at 2 hours | OD at 120 hours |
|---|---|---|---|---|
| Control | 0.004 | 0.006 | 0.008 | 1.828 |
| Example 2 | 0.070 | 0.080 | 0.080 | 0.127 |
| Example 6 | 0.017 | 0.016 | 0.021 | 0.490 |

Example 19

The silver coating prepared in Example 6 was tested for thermal effect when a voltage was applied across the coated substrate using DC power supply (X-Tech). The temperature of the coating was observed using a Fluke Thermal imager. The results are summarized in Table 3 below. Thus, an application of a low voltage to coated filter can heat the filter to as high as 120° C. and offer a mechanism for destroying the microbes colonized or attached to the membrane, renewing its efficacy.

TABLE 3

| Voltage | Current | Temperature of Coating |
|---------|---------|------------------------|
| 1.0 volt | 0.07 Amp | 55° C. |
| 1.3 volt | 0.10 Amp | 72° C. |
| 1.4 volt | 0.13 Amp | 87° C. |
| 1.5 volt | 0.17 Amp | 120° C. |

The invention claimed is:

1. A method for coating a substrate with a metal, said method comprising:
   (a) applying a metal solution to the substrate, wherein the metal solution includes:
      (i) a solvent, and
      (ii) a metal component selected from one or more organic or inorganic metal salts or one or more organometallic complexes of metal,
      wherein the substrate is wettable by the solvent, and the metal component is soluble in the solvent, such that the metal component is absorbed on the substrate;
   (b) subsequent to step (a), reacting at ambient temperature the metal solution at the substrate with a conversion agent to form a metal hydroxide or a metal oxide; and
   (c) exposing the metal hydroxide or metal oxide at the substrate to a plasma environment at ambient temperature and less than 100 KPa pressure to reduce the metal hydroxide or metal oxide to a metal coating at the substrate.

2. The method as in claim 1 wherein the metal solution includes water as the solvent and one or more inorganic metal salts as the metal component.

3. The method as in claim 2 wherein the one or more metal salts are selected from at least one of a sulfate, a nitrate, a carbonate, a bicarbonate, a formate, an acetate, a propionate, a perfluoroacetate, a sulfite, a borate, an arsenate, a chloride, a chlorate, a chromate, and a phosphate.

4. The method as in claim 3 wherein the substrate is cellulose, porous polyether sulfone, porous polybenzimidazole, porous glass, or porous ceramic.

5. The method as in claim 1 wherein the metal solution includes an organic solvent and an organometallic salt or complex of metal as the metal component.

6. The method as in claim 5 wherein the organometallic complex of metal is selected from at least one of copper trifluoroacetylacetonate and silver trifluoroacetate.

7. The method as in claim 1, including applying the metal solution to the substrate by spray coating or dip coating.

8. The method as in claim 1 wherein the conversion agent is selected from at least one of an alkali metal hydroxide.

9. The method as in claim 1 wherein the plasma environment is generated by applying electromagnetic energy in a glow zone between spaced apart electrodes in the presence of a plasma supporting gas selected from the group consisting of argon, hydrogen, krypton, xenon, helium, nitrogen, oxygen, and mixtures thereof.

10. The method as in claim 9 wherein the electromagnetic energy is applied at 13.56 MHz.

11. The method as in claim 1 wherein said metal coating exhibits a surface resistivity of less than $1\times10^5$ $\Omega/\square$.

12. The method as in claim 1, including, subsequent to step (b), drying the substrate to remove the solvent.

* * * * *